(12) United States Patent
Wang et al.

(10) Patent No.: US 11,969,481 B2
(45) Date of Patent: Apr. 30, 2024

(54) DEVICE FOR COLLECTING AND CULTURING FISH EMBRYOS AND METHOD FOR EVALUATING COMBINED TOXICITY OF THIAMETHOXAM AND TETRACONAZOLE

(71) Applicant: Zhejiang Academy of Agricultural Sciences, Hangzhou (CN)

(72) Inventors: Yanhua Wang, Hangzhou (CN); Shanshan Di, Hangzhou (CN); Guiling Yang, Hangzhou (CN); Zhiheng Zhang, Hangzhou (CN); Xinquan Wang, Hangzhou (CN); Qiang Wang, Hangzhou (CN)

(73) Assignee: ZHEJIANG ACADEMY OF AGRICULTURAL SCIENCES, Hangzhou (CN)

( * ) Notice: Subject to any disclaimer, the term of this patent is extended or adjusted under 35 U.S.C. 154(b) by 754 days.

(21) Appl. No.: 16/944,169

(22) Filed: Jul. 31, 2020

(65) Prior Publication Data

US 2021/0299282 A1 Sep. 30, 2021

(30) Foreign Application Priority Data

Mar. 26, 2020 (CN) .......................... 202010221537.6

(51) Int. Cl.
*C12M 1/34* (2006.01)
*A01K 61/10* (2017.01)
(Continued)

(52) U.S. Cl.
CPC .......... *A61K 49/0008* (2013.01); *A01K 61/10* (2017.01); *A61D 1/10* (2013.01);
(Continued)

(58) Field of Classification Search
CPC ...... A61K 49/0008; A01K 61/10; A61D 1/10; C12M 25/02; C12M 25/04; C12M 1/125;
(Continued)

(56) References Cited

U.S. PATENT DOCUMENTS 3,682,138 A * 8/1972 Day ....................... A01K 61/59
119/205
2017/0166853 A1* 6/2017 Ekeroth ................. C12M 25/04

FOREIGN PATENT DOCUMENTS

EP 0415307 A2 * 6/1991 ................ B01L 9/06

OTHER PUBLICATIONS

E. Lammer et al.; "Is the fish embryo toxicity test (FET) with the zebrafish a potential alternative for the fish acute toxicity test?"; Dec. 3, 2008; Elsevier; Comparative Biochemistry and Physiology, Part C (Year: 2008).*

* cited by examiner

*Primary Examiner* — Paul S Hyun
*Assistant Examiner* — Jonathan E Lepage
(74) *Attorney, Agent, or Firm* — Bayramoglu Law Offices LLC

(57) ABSTRACT

A device and a method are disclosed for collecting and culturing fish embryos and evaluating combined toxicity of thiamethoxam and tetraconazole. An embryo collection component and an embryo culture component are provided on a base plate. The embryo collection component includes a collection tray detachably connected to a bottom of a culture tube. The embryo culture component includes a cavity plate with a stopper inside and a top plate provided with a culture well. A bottom of the culture well is provided with a leakage hole; and after the top plate is installed into the cavity plate, the stopper occludes the leakage hole. The new device is used to carry out the combined toxicity effect test of thiamethoxam and tetraconazole on zebrafish (Continued)

embryos, which can be used to avoid development of pesticide mixtures that have a good preventive effect but pose increased toxicity risk to the ecological environment.

12 Claims, 3 Drawing Sheets

(51) Int. Cl.
- *A61D 1/10* (2006.01)
- *A61K 49/00* (2006.01)
- *C12M 1/12* (2006.01)
- *C12M 3/00* (2006.01)
- *C12N 5/073* (2010.01)
- *C12N 15/873* (2010.01)
- *C12Q 1/20* (2006.01)
- *C12Q 1/24* (2006.01)

(52) U.S. Cl.
CPC ............ *C12M 21/08* (2013.01); *C12M 25/02* (2013.01); *C12N 5/0604* (2013.01); *C12N 15/873* (2013.01); *Y02A 40/81* (2018.01)

(58) Field of Classification Search
CPC ...... C12M 23/12; C12N 5/0604; Y02A 40/81; B01L 9/00; B01L 3/5085
See application file for complete search history.

DEVICE FOR COLLECTING AND CULTURING FISH EMBRYOS AND METHOD FOR EVALUATING COMBINED TOXICITY OF THIAMETHOXAM AND TETRACONAZOLE

CROSS REFERENCES TO THE RELATED APPLICATIONS

This application is based upon and claims priority to Chinese Patent Application No. 202010221537.6, filed on Mar. 26, 2020, the entire contents of which are incorporated herein by reference.

TECHNICAL FIELD

The present invention relates to a method for evaluating combined toxicity of pesticides, and more specifically, to a device for collecting and culturing fish embryos and a method for evaluating combined toxicity of thiamethoxam and tetraconazole.

BACKGROUND

The emergence of neonicotinoid insecticides is a milestone innovation in the history of chemical pesticide development. At present, thiamethoxam in this class of insecticides has become the most widely used insecticide in the world. At the initial stage of use, thiamethoxam was considered to have less impact on the environment due to its low dosage and superior effect to previous organophosphorus and carbamate insecticides. After extensive use of thiamethoxam in agricultural production, however, the toxic and side effects of thiamethoxam on the ecological environment gradually became manifest. In fact, it has been considered an important contributing factor causing the colony collapse disorder (CCD) of bees in the worldwide.

When thiamethoxam is used in crop protection, only 1.6% to 20% of the active ingredients are actually used by crops, and the remaining 80% to 98.4% enter the environment. Research shows that thiamethoxam has strong stability and is not easily biodegraded in water. Although the insecticide is not directly used in water, it has extremely high water-solubility and strong potential for leaching and migration. The insecticide easily penetrates into the water environment through surface runoff and groundwater and can accumulate over long periods. Thus, it affects the water ecological environment and human health.

In recent years, thiamethoxam has been frequently detected in water bodies at home and abroad, including the United States, Netherlands, Vietnam, and other countries. Detected amounts are found to have exceeded the water quality standards of various countries causing adverse effects on a variety of aquatic organisms, including species of fish. Although substantial research has been performed on the toxicity effects of thiamethoxam on honeybees, the potential adverse effects of thiamethoxam on the aquatic environment are lacking in-depth understanding. In farmland water, thiamethoxam usually interacts with other pollutants to compound the polluting effect, which poses a serious threat to aquatic organisms, the food chain and human beings. Of equal concern with insecticides for their potentially harmful ecologic effect are certain fungicides.

Triazole fungicides are the second most prolific fungicide category. Once humans developed benzimidazole fungicides, they have become the most widely used fungicides in the world. Some varieties of triazole fungicides have strong environmental stability, reproductive toxicity and endocrine disrupting properties. With the widespread use of such agents, more and more triazole fungicides enter the environment through spray drift, foliage rolling and leaching when used in farm operations. These fungicides, therefore, also pose a serious threat to the ecological environment and human health.

Tetraconazole belongs to the triazole family of fungicides, which have good systemicity and persistence and wide antimicrobial spectrum. Additionally, tetraconazole can be used in various applications, not only for stem and leaf treatment, but also for seed treatment. With the large-scale use of tetraconazole in agricultural production, it has also produced serious toxic and side effects on the ecological environment. For example, a combination of seven pesticides, such as tetraconazole and acetamiprid, can produce synergistic toxicity effects on honeybees. Therefore, carrying out studies on the ecotoxicology of tetraconazole has an important predictive role in reducing its adverse effects on the ecological environment. In this connection, certain organisms are useful for study.

Zebrafish (*Danio rerio*) tops the aquatic biological chain and is a very promising aquatic biological model for toxicological research. At present, zebrafish has been listed as a standard indicator organism for environmental toxicity testing by international organizations such as the International Organization for Standardization (ISO), the Organization for Economic Cooperation and Development (OECD) and the European Economic Community (EEC) and the Ministry of Agriculture of China. Zebrafish embryos have the characteristics of large quantity and easy availability in vitro development, transparency, and short development cycle. The changes of all their internal organs and structures throughout their entire growth process can be observed and studied. At present, zebrafish embryos are widely used in the toxicity evaluation of pollutants. In addition, embryo toxicity tests avoid killing animals or dissecting animals, which is in accordance with the development direction of environmental toxicology: to seek alternative test materials for the protection of animal rights. Therefore, zebrafish embryos have become a favorite subject for study in the field of environmental toxicology.

In recent years, due to climate change and intensive farming, crop diseases and insect pests have become increasingly prevalent. Chemical pesticide use is more frequent as a result. Different pesticides have to be used to control pests and diseases in different growing seasons of crops. In addition, in agricultural production, in order to delay the occurrence of drug resistance, it is recommended to use pesticides with different mechanisms of action alternately, or to save time and labor, various pesticides are used together. For example, neonicotinoid insecticides and triazole fungicides are usually used in combination to expand the control targets and improve the control effect on pests. Because of widespread and frequent combined use of neonicotinoid insecticides and triazole fungicides, mixtures of these two agents usually occur in the actual environment. As a result, research on their single toxicity effects in the past cannot meet actual requirements. Although the single toxicity effects of thiamethoxam and tetraconazole on environmental organisms have been studied and reported, toxicity effects on environmental organisms when the two are combined have not.

SUMMARY

In view of the above-mentioned prior art, the present invention provides a device for collecting and culturing fish embryos and a method for evaluating combined toxicity of thiamethoxam and tetraconazole. In the present invention, a combined toxicity effect test of thiamethoxam and tetraconazole on zebrafish embryos is carried out to provide a scientific basis for the scientific mixed use of neonicotinoid insecticides and triazole fungicides, so as to avoid the development of pesticide mixtures that have a good control effect but at the same time have a higher toxicity risk to the ecological environment.

In order to achieve the above objective, the technical solution adopted by the present invention is to provide a device for collecting and culturing fish embryos and a method for evaluating combined toxicity of thiamethoxam and tetraconazole. The device for collecting and culturing fish embryos in the present invention includes a base plate. A snap-fit hole is provided on the base plate, and an embryo collection component and an embryo culture component are snap-fitted in the snap-fit hole.

The embryo collection component includes a culture tube and a collection tray. Two ends of the culture tube are open. A bottom of the culture tube is provided with a filter screen and an inner wall of the culture tube is provided with a snap-fit slot. A partition is movably inserted in the snap-fit slot, and the partition divides the culture tube into a left culture cavity and a right culture cavity with equal volumes. The collection tray is detachably connected to the bottom of the culture tube.

The embryo culture component includes an embryo culture plate, and the embryo culture plate includes a cavity plate and a top plate. A stopper is provided in the cavity plate. A culture well recessed downward is provided on the top plate. A leakage hole is provided at a bottom of the culture well, and after the top plate is installed into the cavity plate, the stopper removable occludes the leakage hole.

The device of the present invention integrates the fish embryo collection component and the embryo culture component. The embryos can be cultured after the embryo collection is completed, and the operation is more convenient and faster. In the present invention, the fish embryo collection component includes a culture tube and a collection tray. An internal space of the culture tube can be divided into two parts of a left culture cavity and a right culture cavity by a movable partition, which is convenient for isolation breeding of brood fish of different genders. The male and female brood fish can be mixed by removing the partition. Without manual transshipment, the brood fish are better able to survive and spawning rates can also be maintained at a high level. The filter screen provided at the bottom of the culture tube restricts the brood fish to only move in the culture tube, and fertilized embryos fall into the collection tray to avoid damage to the embryos typically caused by the swimming of the brood fish. The collection tray and the culture tube are connected in a detachable manner, and the embryo collection component is easy to assemble, which is convenient for retrieval of embryos.

The embryo culture component in the present invention includes an embryo culture plate, and the embryo culture plate includes a cavity plate and a top plate. The cavity plate provides an installation space for the top plate, and a leakage hole is provided at the bottom of the culture well on the top plate. When the top plate is installed into the cavity plate, the leakage hole is blocked by the stopper installed in the installation cavity of the cavity plate. At this time, the culture medium can be added to culture the embryos. When the culture medium needs to be replaced, the top plate can be pulled up, and the original culture medium flows into the cavity plate through the leakage hole. The culture medium in all culture wells can be discharged at one time, avoiding syphoning one by one, saving significant time and labor.

Based on the above technical solutions, the device for collecting and culturing fish embryos of the present invention can be further improved as follows.

Further, a depth of the snap-fit hole is smaller than a height of the collection tray and a height of the cavity plate.

In the present invention, the depth of the snap-fit hole is set to be smaller than the height of collection tray and the cavity plate. After the collection tray and the cavity plate are installed in the snap-fit hole, a part of the collection tray and the cavity plate are exposed from the snap-fit hole, making the fetching and placing of the collection tray and the cavity plate more convenient and effortless.

Further, mesh diameters of the filter screen are larger than diameters of the fish embryos and smaller than body lengths of the fish.

By restricting the mesh size of the filter screen, the activity range of the brood fish can be limited to the culture tube, and the produced fertilized embryos can fall into the collection tray, which can avoid the negative impact of the swimming of the brood fish on the embryos.

Further, the collection tray and the culture tube are connected in a threaded manner.

The collection tray and the culture tube are connected in a threaded manner, which not only has optimal waterproofing, ensuring that water will not flow out from the connection joint, but also makes assembly more convenient and faster.

Further, a diameter of the leakage hole increases gradually from top to bottom, and a diameter of the stopper decreases gradually from top to bottom.

By setting the shape of the leakage hole and the stopper to the above-mentioned form, the contact area between the leakage hole and the stopper can be increased, and the water-tight sealing of the connection joint can be increased to avoid the leakage of the culture medium from the culture well during the culture process.

Further, an enclosure is provided at a bottom of the top plate, and a size of the enclosure is equivalent to a size of the upper cavity on the cavity plate.

In the present invention, an enclosure is provided at the bottom of the top plate, which can ensure the installation stability of the top plate and avoid any disturbance during the culture process which may affect the growth of the embryos.

Further, a hanging edge is provided outside the enclosure.

The hanging edge can fix the position of the top plate, and can also be used as a stress point to facilitate the assembly and disassembly of the top plate.

The device for collecting and cultivating fish embryos of the present invention can be used for fish embryo culture and other experiments. In the present invention, the device was used to evaluate the combined toxicity of thiamethoxam and tetraconazole. The specific method includes the following steps:

S1: collecting embryos of fertilized fish;

S2: after collecting the embryos for 3 hours, selecting the normally divided embryos and loading them into the culture wells in an amount of 10 embryos per well, and adding a pesticide solution containing thiamethoxam and/or tetraconazole to submerge the embryos, when the pesticide solution contains both thiamethoxam and tetraconazole, a concentration ratio of the thiamethoxam and the tetraconazole is ranging from 81:1 to 1:81; and then controlling an environment temperature to be 26° C. to 28° C. for conducting a toxicity exposure;

S3: replacing the pesticide solution in the culture well with a fresh pesticide solution every 24 hours, and removing the dead embryos in time;

S4: finishing the toxicity exposure after 96 hours, and calculating the mortality M according to formula (I), $$M = (D/N) \times 100\% \quad (I)$$

in formula (I), D is the number of dead embryos and N is the total number of embryos;

S5: calculating the 50% lethal concentration $LC_{50}$ and 95% confidence limits of the fish embryos according to the mortality M; then calculating the sum S of biotoxicity of the pesticide solution according to formula (II), $$S = A_m/A_i + B_m/B_i \quad (II)$$

in formula (II), $A_m$ and $B_m$ are the 50% lethal concentration $LC_{50}$s of the thiamethoxam and the tetraconazole respectively when used in combination, and $A_i$ and $B_i$ are the $LC_{50}$s of the thiamethoxam and the tetraconazole respectively when used alone.

S6: converting the sum S of biotoxicity of the pesticide solution into an additive index AI according to formula (III), $$AI = \begin{cases} 1/S - 1, & S \leq 1 \\ 1 - S, & S > 1 \end{cases} \quad (III)$$

judging the combined effect of the thiamethoxam and the tetraconazole according to the value of the additive index AI; when AI≥0.25, a synergistic effect is judged, when −0.2<AI<0.25, an additive effect is judged, and when AI≤0.2, an antagonistic effect is judged.

The method of the present invention can be used to evaluate the combined toxicity effect of thiamethoxam and tetraconazole on zebrafish embryos, thereby providing a scientific basis for the scientific combined use of neonicotinoid insecticides and triazole fungicides, and avoiding the development of pesticide mixtures that have a good control effect, but at the same time have a higher toxicity risk to the ecological environment.

The evaluation method in the present invention can be further improved as follows on the basis of the above technical solutions.

Further, the collecting embryos of fertilized fish in step S1 includes the following steps: placing the adult female brood fish and the adult male brood fish into the left culture cavity and the right culture cavity of the culture tube respectively one night in advance, with a ratio of the number of the female brood fish to the male brood fish of 1:2; then pulling out the partition at dawn the next morning, and then collecting the embryos 30 minutes later.

The advantages of the present invention are as follows.

1. The device of the present invention integrates the embryo collection component and the embryo culture component. The embryos can be cultured after the collection is complete, and the operation is more convenient and faster.

The device can provide a good environment for the study of the toxicity effects of pesticide exposure on the zebrafish embryos. The results are more accurate.

2. The method for evaluating the combined toxicity of thiamethoxam and tetraconazole to zebrafish embryos in the present invention provides a reference for the toxicity test of the combined exposure of other different kinds of pollutants to zebrafish embryos, and provides important scientific basis for the monitoring and early warning of the combined pollution of pesticides in water bodies and agricultural products.

Figure 1:
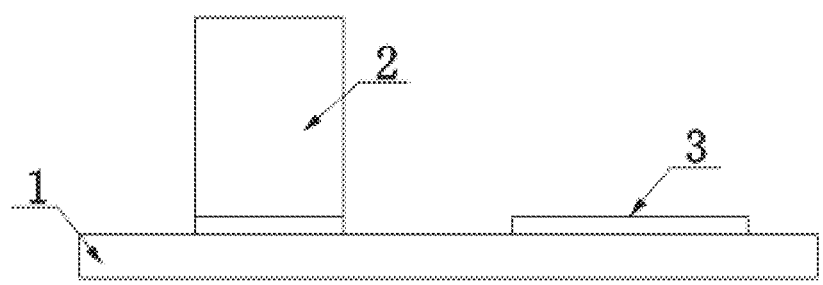
FIG. 1 is a front view of the device of the present invention.

Key for reference numerals: 1. base plate; 11. snap-fit hole; 2. embryo collection component; 21. culture tube; 22. collection tray; 23. filter screen; 24. snap-fit slot; 25. partition; 3. embryo culture component; 31. cavity plate; 32. top plate; 33. stopper; 34. culture well; 35. leakage hole; 36. enclosure; and 37. hanging edge.

DETAILED DESCRIPTION OF THE EMBODIMENTS

The device of the present invention is described in detail below with reference to the drawings.

Figure 2:
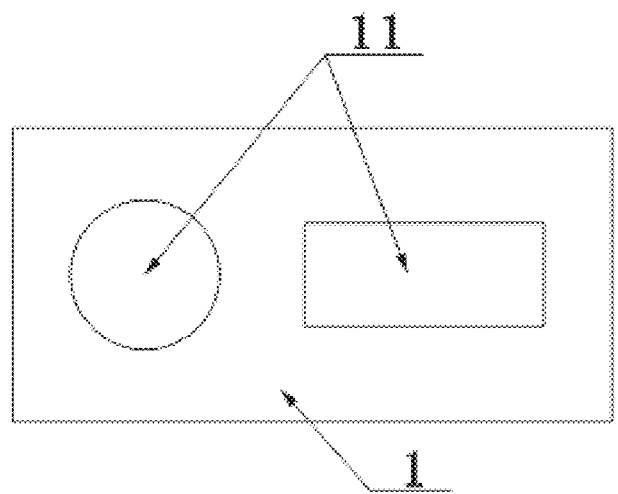
FIG. 2 is a top view of the base plate.

The structure of the device for collecting and culturing fish embryos of the present invention is shown in FIGS. 1-4. The device includes the base plate 1. The base plate 1 is made of a hard material such as hard plastic or stainless steel with a regular geometric shape, such as a circle, a square, or other shapes. As shown in FIG. 2, the snap-fit hole 11 is provided on the surface of the base plate 1, and the embryo collection component 2 and the embryo culture component 3 are snap-fitted in the snap-fit hole 11.

Figure 3:
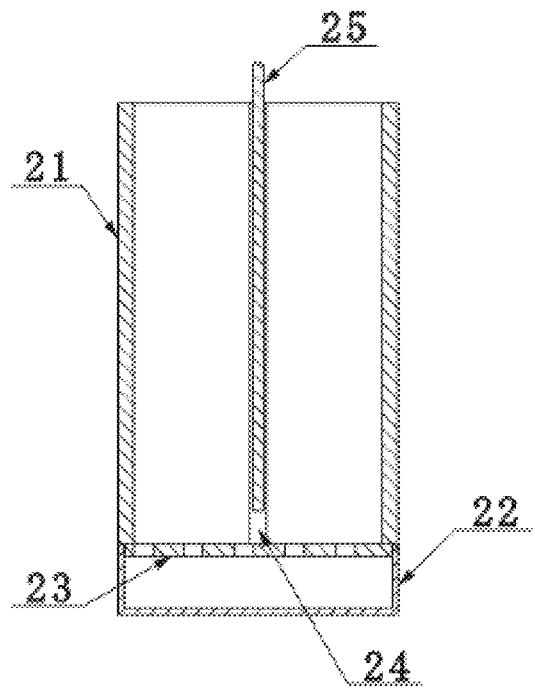
FIG. 3 is a cutaway view of the embryo collection component.

As shown in FIG. 3, the embryo collection component 2 includes the culture tube 21 and the collection tray 22. The culture tube 21 has a generally cylindrical shape, and is made of transparent materials such as glass, polymethyl methacrylate, and the like. The two ends of the culture tube 21 are open, and the bottom of the culture tube 21 is provided with the filter screen 23 by snap-fitting, bonding, or other manners. The inner wall of the culture tube 21 is provided with the snap-fit slot 24, and the partition 25 is movably inserted in the snap-fit slot 24. The partition 25 is made of the same material as the culture tube 21. After inserting the partition 25, the internal space of the culture tube 21 is divided into two parts, a left cavity and a right cavity with equal volumes. The collection tray 22 is made of the same material as the culture tube 21 and is detachably connected to the bottom of the culture tube 21.

In order to increase the water-tight sealing of the connection joint between the collection tray 22 and the culture tube 21, and at the same time facilitate the disassembly and assembly, the collection tray 22 and the culture tube 21 are connected in a threaded manner. In addition, in order to make the embryos of the fertilized fish only fall into the collection tray 22, and at the same time limit the activity range of the brood fish to the culture tube 21, and avoid the adverse effects on the embryos caused by the swimming of the brood fish, it is preferable to set the mesh diameters of the filter screen 23 larger than the diameters of the fish embryos and smaller than the body lengths of the fish. After the assembly of the embryo collection component 2 is completed, the embryo collection component 2 is snap-fitted to the corresponding snap-fit hole 11 on the base plate 1, and the snap-fit hole 11 corresponding to the embryo collection component 2 is circular. The collection tray 22 is directly in contact with the snap-fit hole 11. In order to fetch and place the collection tray 22 conveniently, the depth of the snap-fit hole 11 is preferably smaller than the height of the collection tray 22.

In a preferred embodiment of the present invention, a water outlet with a bag valve is provided on the side wall of the lower end of the culture tube 21, and after collecting the embryos, the water in the culture tube 21 is discharged through the water outlet to facilitate the disassembly of the embryo collection component.

Figure 4:
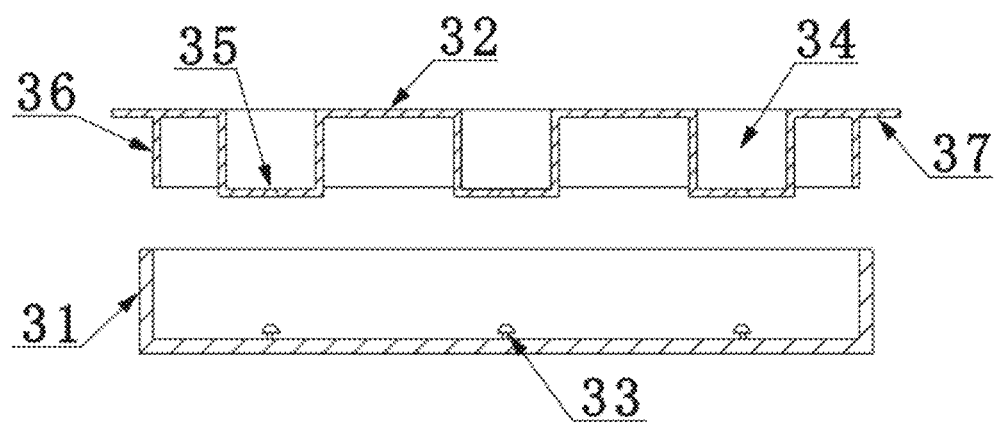
FIG. 4 is a cutaway view of the embryo culture component.

As shown in FIG. 4, the embryo culture component 3 includes an embryo culture plate. The embryo culture plate includes a cavity plate 31 and a top plate 32. The cavity plate 31 and the top plate 32 are made of the same materials as the conventional cell culture plate, and have a square shape as a whole. A cavity recessed downward is provided on the top surface of the cavity plate 31, and the stopper 33 is provided in the cavity of the cavity plate 31 by bonding, welding, or other manner. The top surface of the top plate 32 is provided with a culture well 34 recessed downward, the number of the culture wells 34 is not less than 6, and the bottom of each of the culture wells 34 is provided with the leakage hole 35. The top plate 32 may be installed into the cavity of the cavity plate 31, and the stopper 33 removably occludes the leakage hole 35 after the top plate 32 is installed into the cavity plate 31. In order to avoid the leakage of the culture medium through the leakage hole 35 during the embryo culture, it is preferable to set the leakage hole 35 as a irregularly-shaped hole to increase the contact area between the leakage hole 35 and the stopper 33, thereby improving the sealing effect.

In a preferred mode of the present invention, the leakage hole 25 has an inverted trapezoid shape, that is, the diameter of the leakage hole 25 gradually increases from top to bottom, and correspondingly, the diameter of the stopper 23 gradually decreases from top to bottom. After the assembly of the embryo culture component 3 is completed, the embryo culture component 3 is placed in the corresponding snap-fit hole 11 on the base plate 1, and the snap-fit hole 11 corresponding to the embryo culture component 3 is square. The cavity plate 31 directly contacts the snap-fit hole 11. In order to facilitate fetching and placing of the cavity plate 31, the depth of the snap-fit hole 11 is preferably smaller than the height of the cavity plate 31.

In a preferred embodiment of the present invention, the enclosure 36 is provided at the bottom of the top plate 32, the enclosure 36 encloses the culture well 34, and the size of the enclosure 36 is equivalent to the size of the upper cavity on the cavity plate 31. When installing the top plate 32, the enclosure 36 serves as a guide part to make the top plate 32 more easily to inserted into the cavity plate 31. Meanwhile, the enclosure 36 can limit the movement of the top plate 32 to make the installation more stable and avoid unnecessary shaking which may affect the normal development of the embryos. In addition, in order to facilitate the assembly and disassembly of the top plate 32, the hanging edge 37 is provided outside the enclosure 36.

The device of the present invention has a simple structure and is easy to operate, and can be used for the toxicity evaluation of various pesticides. The present invention further develops a method for evaluating the combined toxicity of thiamethoxam and tetraconazole by using the designed device for collecting and culturing fish embryos. The procedure of the method is described in detail in combine with the following embodiments.

1. Experimental Materials

1. Test Organism

The wild-type AB strain adult zebrafish is purchased from the Institute of Hydrobiology, Chinese Academy of Sciences (Wuhan, China). Adult male and female zebrafish are cultured separately in water cycle aquaculture systems (Beijing Environ Science Development Co., Ltd., Beijing, China). The water temperature is controlled at 27±1° C., and the photoperiod is composed of 14 hours of light and 10 hours of dark. The zebrafish are fed with fresh fairy shrimp larvae to the zebrafish 2 to 3 times a day, and the larvae are hatched from the eggs of fairy shrimp. During hatching, the eggs of fairy shrimp are placed in 25 $g \cdot L^{-1}$ sodium chloride solution with a water temperature of 27±1° C., and continuous aeration and illumination is provided for 32 hours, and then the larvae are hatched out. Subsequently, the larvae are collected, and impurities are removed and excessive salt is removed with clean water. The larvae can be stored in a refrigerator at 4° C. for a short time, or frozen at −20° C.

Method for collecting zebrafish embryos: the embryo collection component of the present invention is assembled; and then the adult female and male brood fish are loaded into the left culture cavity and the right culture cavity of the culture tube 21 separately one night in advance, and the ratio of the number of female brood fish to male brood fish is 1:2. At dawn the next morning, the partition 25 is pulled out and the embryos are collected 30 minutes later. After the embryo collection is completed, the culture tube 21 and the collection tray 22 are separated, the collection tray 22 is taken out. The embryos in the collection tray is rinsed with water then replaced with clean fish farming water, and then the embryos are used as experimental materials.

1.2 Pesticides and Reagents

The tested pesticides are thiamethoxam and tetraconazole active pharmaceutical ingredient (API), with a purity of greater than 95%. Tween 80 and N,N-dimethylformamide (DMF) are both analytically pure. The tested APIs are formulated into high concentration stock solutions with the tween-80 and the N,N-dimethylformamide. During the test, a certain amount of pesticide stock solution is taken and diluted step-by-step with standard dilution water by a serial dilution method with a geometrical ratio to obtain 5 to 7 of required concentrations. The drug solution was obtained.

The test water during the test is an oxygen saturated standard dilution water prepared uniformly. Each liter of water contains 294.0 $mg \cdot L^{-1}$ $CaCl_2 \cdot 2H_2O$, 123.3 $mg \cdot L^{-1}$ $MgSO_4 \cdot 7H_2O$, 63.0 $mg \cdot L^{-1}$ $NaHCO_3$ and 5.5 $mg \cdot L^{-1}$ KCl.

Embodiment 1: Toxicity Test for Single Pesticide

In the present embodiment, the effect of a single pesticide on the development embryos of fertilized fish is evaluated. The evaluation method includes the following steps:

S1: The embryo culture component 3 is assembled; toxicity exposure is performed after 3 hours post-fertilization (3 hpf) of embryos; after collecting the zebrafish embryos for 3 hours, the abnormal and dead embryos are removed, and the normally divided embryos are picked out under an inverted microscope, and the selected embryos are loaded in into the culture well 34 in an amount of 10 embryos per well; after removing the water as much as possible, 10 mL of single pesticide solution with different concentrations are added to each well in the treatment group separately, and an equal volume of standard dilution water is added to the blank control group and the solvent control group, respectively. Three replicates are set for each treatment group, blank control group and solvent control group, and every 2 wells are served as one replicate, that is, 20 embryos are one replicate. Each test pesticide is set with 5 to 7 concentrations using serial dilution method with a geometrical ratio, and each concentration is set with three repeats.

S2: The semi-static method is used, that is, the medium in the wells are replaced with fresh pesticide solution every 24 hours, and the dead embryos are picked out in time. When the medium is replaced with the fresh pesticide solution, the top plate 32 is pulled up, the original culture medium flows through the leakage hole 35 into the cavity of the cavity plate 31, and then the original culture medium is poured out together. Then, the top plate 32 is mounted on the cavity plate 31, and the fresh pesticide solution is added to the culture well 34 loaded with embryos.

Figure 5:
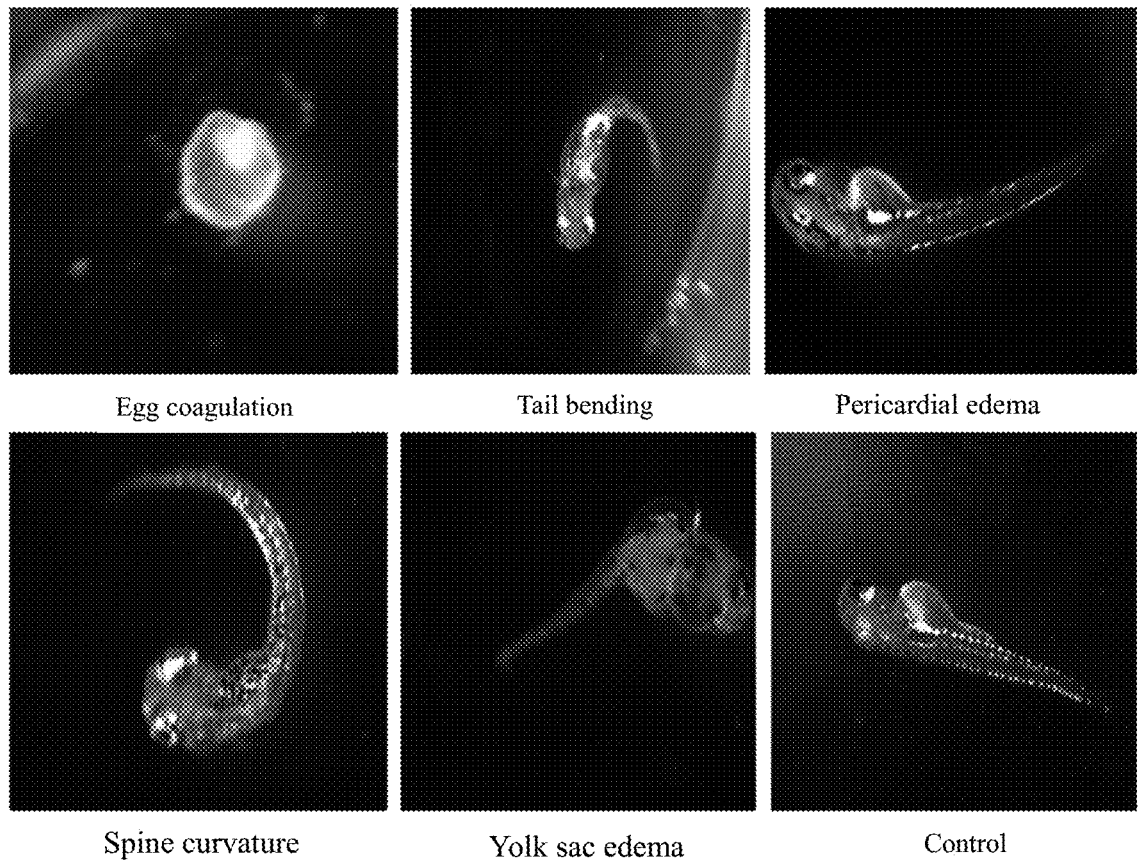
FIG. 5 shows poisoning symptoms of zebrafish embryos.

S3: After 96 hours of toxicity exposure, the embryo mortality and poisoning symptoms are recorded. Embryo death was characterized by egg coagulation, somite disruption, non-detachment of tail or lack of heartbeat; common symptoms of embryo poisoning include the following deformities: egg coagulation, pericardial edema, yolk sac edema, spine curvature, tail bending, and others (FIG. 5). The mortality M is calculated according to the formula (I), $$M = (D/N) \times 100\%. \tag{I}$$

In formula (I), D is the number of dead embryos and N is the total number of embryos. DPS statistical analysis software (version number: V15.10) is used to statistically analyze the mortality data of zebrafish embryos with the probabilistic value analysis method, and the 50% lethal concentration $LC_{50}$ and 95% confidence limits of the fish embryos are calculated.

Embodiment 2: Toxicity Test for Combined Pesticides

In the past, the research on the combined effect of pesticides was usually carried out by the method of equal toxicity and equal concentration, but in the actual environment, it is rare that pesticides are mixed in equal toxicity or equal concentration. In the present invention considering that the concentration ratio of the mixed pesticide in the water environment changes at different times and in different regions, and nine different concentration ratios are measured, namely 81:1, 27:1, 9:1, 3:1, 1:1. 1:3, 1:9, 1:27 and 1:81, which can basically cover the concentration ratio of the two pesticides in the actual environment. In the present embodiment, the method for evaluating the toxicity of the combined pesticide includes the steps as follows.

S1: The embryo culture component 3 is assembled; toxicity exposure is performed after 3 hours post-fertilization (3 hpf) of embryos; after collecting the zebrafish embryos for 3 hours, the abnormal and dead embryos are picked out under an inverted microscope, and the selected embryos are loaded in into the culture well 34 in an amount of 10 embryos per well; after removing the water as much water as possible, 10 mL of different concentrations of the combined pesticide solution are added to each well in the treatment group separately, and an equal volume of standard dilution water is added to the blank control group and the solvent control group, respectively. Three replicates are set for each treatment group, blank control group and solvent control group, and every 2 wells are served as one replicate, that is, 20 embryos are one replicate. The mixed pesticide with each concentration ratio is set with 5 to 7 concentrations using serial dilution method with a geometrical ratio, and each concentration is set with three repeats.

S2: The semi-static method, that is, the medium in the wells are replaced with fresh pesticide solution every 24 hours, and the dead embryos are picked out in time. When the medium is replaced with the fresh pesticide solution, the top plate 32 is pulled up, the original culture medium flows through the leakage hole 35 into the cavity of the cavity plate 31, and then the original culture medium is poured out together. Then, the top plate 32 is mounted on the cavity plate 31, and the fresh pesticide solution is added to the culture well 34 loaded with embryos.

S3: After 96 hours of toxicity exposure, the embryo mortality and poisoning symptoms are recorded. The mortality M is calculated according to the formula (I), $$M = (D/N) \times 100\%. \tag{I}$$

In formula (I), D is the number of dead embryos and N is the total number of embryos. DPS statistical analysis software (version number: V15.10) is used to statistically analyze the mortality data of zebrafish embryos with the probabilistic value analysis method, and the 50% lethal concentration $LC_{50}$ and 95% confidence limits of the fish embryos are calculated.

Embodiment 3 Evaluation the Combined Toxicity of the Pesticides

In the present embodiment, the data obtained in Embodiment 1 and Embodiment 2 are used to evaluate the toxicity effect of combined exposure of thiamethoxam and tetraconazole on zebrafish embryos. The evaluation method is the improved Marking Addition Index Method.

In order to evaluate the combined toxicity of the thiamethoxam and the tetraconazole, the concept of the sum of biotoxicity (S) is introduced, and the sum of biotoxicity S is calculated using the formula (II):

$$S = A_m/A_i + B_m/B_i. \tag{II}$$

In formula (II), $A_m$ and $B_m$ are the toxicity (50% lethal concentration $LC_{50}$) of the thiamethoxam and the tetraconazole in the combined pesticides respectively, and $A_i$ and $B_i$ are the toxicity (50% lethal concentration $LC_{50}$) of the thiamethoxam and the tetraconazole respectively when used alone. After calculating the sum of biotoxicity S, the sum of biotoxicity S of the pesticides is converted into an additive index AI according to formula (III), $$AI = \begin{cases} 1/S - 1, & S \leq 1 \\ 1 - S, & S > 1 \end{cases}, \tag{III}$$

Finally, the AI value is used to evaluate the combined effect of pesticides. When −0.2<AI<0.25, it is evaluated as additive effect; when AI≥0.25, it is evaluated as synergism effect; and when AI≤−0.2, it is evaluated as antagonistic effect.

Since AI=0 is the additive effect in the Marking additive index method, and in practical studies, AI=0 rarely occurs. In this study, when −0.2<AI<0.25, the evaluation result is additive effect, and the method of setting the AI value into an interval and defining it as additive effect is more consistent with the actual situation.

Result Analysis

The total fertilization rate of embryos used in this experiment was greater than or equal to 80%. During the experiment, the temperature in the test container was maintained at 25.49° C. to 26.84° C. At the end of the experiment, the embryo survival rate of the blank control group was 93.48±3.16%, and the embryo hatching rate of the blank control group was 86.93±4.37%. The dissolved oxygen contents of solutions of the blank control group and the highest concentration treatment group were greater than or equal to 85.4% of air saturation. The results showed that the test was effective and met the quality control requirements.

The toxicity effect of single pesticide on the zebrafish embryos showed that within the range of measured pesticide concentrations, the embryo mortality rate increased with the increase of the concentration of pesticide. In the treatment group with high concentration of tetraconazole, the poisoning symptoms of embryos such as pericardial edema, yolk sac edema, spine curvature, tail bending, and others were observed (FIG. 5), while in the thiamethoxam treatment group, poisoning symptoms of zebrafish embryos were not obvious. After 96 hours of exposure, the $LC_{50}$ and 95% confidence limits of thiamethoxam and tetraconazole for zebrafish embryos were 246.1 (187.2-353.6) mg a.i. $L^{-1}$ and 10.97 (8.23-15.69) mg a.i. $L^{-1}$, respectively, when used alone, suggesting that the toxicity of single exposure of tetraconazole to zebrafish embryos was significantly greater than that of the single exposure of thiamethoxam (Table 1).

The toxicity results of combined pesticides on the zebrafish embryos showed that: when the thiamethoxam and the tetraconazole were mixed in different concentrations, the AI value of the toxicity to zebrafish embryos ranged from 1.41 to 6.19, that is, the toxicity increased by 2.41 to 7.19 fold, suggesting that these two pesticides have a significant synergistic toxicity effect on zebrafish embryos, that is, when the two pesticides are mixed, the toxicity of the two pesticides to zebrafish embryos increased (Table 1). The mixed treatment group of thiamethoxam and tetraconazole produced poisoning symptoms such as pericardial edema, yolk sac edema, spine curvature, tail bending, and others on zebrafish embryos.

TABLE 1

Combined toxicity effects of thiamethoxam and tetraconazole on zebrafish embryos

| Concen-tration ratio | $LC_{50}$ (95% confidence limit)[b] mg a.i./$L^{-1}$ | | AI[a] Value |
|---|---|---|---|
| | thiamethoxam | tetraconazole | |
| 81:1 | 80.13 (64.27~97.46) | 0.98 (0.79~1.20) | 1.41 |
| 27:1 | 48.27 (39.41~58.14) | 1.78 (1.46~2.15) | 1.78 |
| 9:1 | 21.39 (15.92~27.48) | 2.37 (1.76~3.05) | 2.29 |
| 3:1 | 7.91 (7.04~8.93) | 2.64 (2.34~2.98) | 2.67 |
| 1:1 | 1.46 (0.92~2.03) | 1.46 (0.92~2.03) | 6.19 |
| 1:3 | 0.81 (0.63~1.19) | 2.43 (1.89~3.57) | 3.45 |
| 1:9 | 0.23 (0.17~0.31) | 2.07 (1.53~2.79) | 4.27 |
| 1:27 | 0.079 (0.071~0.091) | 2.13 (1.92~2.46) | 4.14 |
| 1:81 | 0.027 (0.019~0.039) | 2.18 (1.53~3.16) | 4.01 |

[a]Additive index value

The combination of thiamethoxam and tetraconazole under different concentration ratios has a significant synergistic effect on zebrafish embryos, suggesting that the coexistence of thiamethoxam and tetraconazole could pose a serious threat to the water environment and human health. Although the mixture of thiamethoxam and tetraconazole is widely used in agricultural production to improve the control effect on harmful organisms and expand the control spectrum, the combined toxicity can also have potential adverse effects on the ecological environment when the thiamethoxam and the tetraconazole coexist. Therefore, caution should be exercised when using the mixture of thiamethoxam and tetraconazole in agricultural production to avoid serious toxic and side effects.

In the present invention, the toxicity evaluation of the combined exposure of thiamethoxam and tetraconazole to zebrafish embryos is carried out, which provides a reference for the toxicity test of the combined exposure of other different kinds of pollutants to zebrafish embryos, and provides an important scientific basis for the monitoring and early warning of the combined pollution of pesticides in water bodies.

For the purposes of promoting an understanding of the principles of the invention, specific embodiments have been described. It should nevertheless be understood that the description is intended to be illustrative and not restrictive in character, and that no limitation of the scope of the invention is intended. Any alterations and further modifications in the described components, elements, processes or devices, and any further applications of the principles of the invention as described herein, are contemplated as would normally occur to one skilled in the art to which the invention pertains.

What is claimed is:

1. A device for collecting and culturing fish embryos, comprising:
   a base plate,
   snap-fit holes provided on the base plate, and
   an embryo collection component and an embryo culture component wherein the embryo collection component and the embryo culture component are snap-fitted in the snap-fit holes, respectively;
   wherein,
   the embryo collection component comprises a culture tube and a collection tray, two ends of the culture tube are open, a bottom of the culture tube is provided with a filter screen, and an inner wall of the culture tube is provided with a snap-fit slot, a partition is movably inserted in the snap-fit slot, and the partition divides the culture tube into a left culture cavity and a right culture cavity with equal volumes, and the collection tray is detachably connected to the bottom of the culture tube;
   the embryo culture component comprises an embryo culture plate, and the embryo culture plate comprises a cavity plate and a top plate, the cavity plate is provided with a stopper; the top plate is provided with a culture well recessed downward, a bottom of the culture well is provided with a leakage hole, and the stopper blocks the leakage hole after the top plate is installed into the cavity plate.

2. The device for collecting and culturing fish embryos according to claim 1, wherein a depth of each of the snap-fit holes is smaller than a height of the collection tray and a height of the cavity plate.

3. The device for collecting and culturing fish embryos according to claim 1, wherein the collection tray and the culture tube are connected in a threaded manner.

4. The device for collecting and culturing fish embryos according to claim 1, wherein a diameter of the leakage hole increases gradually from top to bottom, and a diameter of the stopper decreases gradually from top to bottom.

5. The device for collecting and culturing fish embryos according to claim 1, wherein a bottom of the top plate is provided with an enclosure, and a size of the enclosure is equivalent to a size of an upper cavity on the cavity plate.

6. The device for collecting and culturing fish embryos according to claim 5, wherein a hanging edge is provided outside the enclosure.

7. A method for evaluating combined toxicity of thiamethoxam and tetraconazole using the device for collecting and culturing fish embryos according to claim 1, comprising the following steps:

S1: collecting embryos of fertilized fish;

S2: after collecting the embryos for 3 hours, selecting and loading divided embryos into a plurality of culture wells in an amount of 10 embryos per well, adding a pesticide solution containing thiamethoxam to a first subset of culture wells to submerge the embryos, adding a pesticide solution containing tetraconazole to a second subset of culture wells to submerge the embryos, and adding a pesticide solution containing thiamethoxam and tetraconazole to a third subset of culture wells to submerge the embryos, wherein each subset of the culture wells contains 5 to 7 different concentrations of pesticide solution, and for the pesticide solution containing both thiamethoxam and tetraconazole, a concentration ratio of the thiamethoxam and the tetraconazole ranges from 81:1 to 1:81; and an environment temperature ranges from 26° C. to 28° C. for conducting a toxicity exposure;

S3: replacing the pesticide solutions in the plurality of culture wells with fresh pesticide solutions every 24 hours, and removing dead embryos in time;

S4: finishing exposure of fish to the pesticide solutions after 96 hours, and calculating a mortality M according to formula (I) for each culture well, $$M = (D/N) \times 100\% \tag{I}$$

in formula (I), D is a number of dead embryos and N is a total number of embryos;

S5: calculating a 50% lethal concentration LC 50 and 95% confidence limits of the fish embryos according to the mortality M for each subset of culture wells; then calculating a sum S of biotoxicity of the pesticide solution according to formula (II), $$S = A_m/A_i + B_m/B_i \tag{II}$$

in formula (II), $A_m$ and $B_m$ are 50% lethal concentration $LC_{50}$s of the thiamethoxam and the tetraconazole respectively when used in combination, and $A_i$ and $B_i$ are $LC_{50}$s of the thiamethoxam and the tetraconazole respectively when used alone;

S6: converting the sum S of biotoxicity of the pesticide solutions into an additive index AI according to formula (III), $$AI = \begin{cases} 1/S - 1, & S \le 1 \\ 1 - S, & S > 1 \end{cases} \tag{III}$$

judging the combined effect of the two thiamethoxam and the tetraconazole according to the value of the additive index AI; when AI≥25, a synergistic effect is judged, when −0.2<AI<0.25, an additive effect is judged, and when AI≤−0.2, an antagonistic effect is judged; and wherein step S1 comprises the following steps: placing adult female brood fish and adult male brood fish into the left culture cavity and the right culture cavity of the culture cavity respectively one night in advance, with a ratio of a number of the female brood fish to a number of the male brood fish of 1:2; then pulling out the partition at dawn of a next morning, and then collecting the fish embryos 30 minutes later.

8. The method according to claim 7, wherein a depth of each of the snap-fit holes is smaller than a height of the collection tray and a height of the cavity plate.

9. The method according to claim 7, wherein the collection tray and the culture tube are connected in a threaded manner.

10. The method according to claim 7, wherein a diameter of the leakage hole increases gradually from top to bottom, and a diameter of the stopper decreases gradually from top to bottom.

11. The method according to claim 7, wherein a bottom of the top plate is provided with an enclosure.

12. The method according to claim 11, wherein a hanging edge is provided outside the enclosure.

* * * * *